(12) United States Patent
Hipol et al.

(10) Patent No.: US 9,022,025 B2
(45) Date of Patent: May 5, 2015

(54) INTEGRATED DIVING SNORKEL AND REGULATOR AND METHODS OF USE

(71) Applicant: Innovatech Engineering, LLC, Tallahassee, FL (US)

(72) Inventors: Philip J. Hipol, Tallahassee, FL (US); David Haldane, Tallahassee, FL (US); Rick Kearney, Tallahassee, FL (US)

(73) Assignee: Innovatech Engineering, LLC, Tallahassee, FL (US)

( * ) Notice: Subject to any disclaimer, the term of this patent is extended or adjusted under 35 U.S.C. 154(b) by 0 days.

(21) Appl. No.: 14/170,240

(22) Filed: Jan. 31, 2014

(65) Prior Publication Data

US 2015/0020799 A1 Jan. 22, 2015

Related U.S. Application Data

(60) Provisional application No. 61/846,829, filed on Jul. 16, 2013.

(51) Int. Cl.
*A61M 16/20* (2006.01)
*B63C 11/22* (2006.01)
*B63C 11/20* (2006.01)
*B63C 11/18* (2006.01)

(52) U.S. Cl.
CPC .......... *B63C 11/2227* (2013.01); *B63C 11/205* (2013.01); *B63C 11/186* (2013.01); *A61M 16/20* (2013.01)

(58) Field of Classification Search
CPC ...... B63C 11/16; B63C 11/165; B63C 11/18; B63C 11/186; B63C 11/20; B63C 11/202; B63C 11/205; B63C 11/207; B63C 11/22; B63C 11/2254; A61M 16/20; A61M 16/0875; A61M 16/0402; A61M 16/0463

USPC ............ 128/200.29, 201.11, 205.24, 204.26, 128/200.24, 200.26; 137/625.21, 625.46, 137/625.41
See application file for complete search history.

(56) References Cited

U.S. PATENT DOCUMENTS

| | | | | |
|---|---|---|---|---|
| 4,304,229 A | * | 12/1981 | Curtin ...................... | 128/201.11 |
| 5,438,977 A | * | 8/1995 | Gomez et al. ............ | 128/202.14 |
| 5,466,228 A | * | 11/1995 | Evans ........................... | 604/248 |
| 5,746,199 A | * | 5/1998 | Bayron et al. ............ | 128/205.24 |
| 7,320,324 B2 | * | 1/2008 | Willeford ................. | 128/207.16 |
| 8,602,058 B1 | * | 12/2013 | Del Castillo ............. | 137/625.47 |
| 2011/0155135 A1 | * | 6/2011 | Chiu ........................ | 128/205.24 |
| 2013/0186402 A1 | * | 7/2013 | Young ...................... | 128/205.12 |

* cited by examiner

*Primary Examiner* — Tan-Uyen (Jackie) T Ho
*Assistant Examiner* — Bradley Philips
(74) *Attorney, Agent, or Firm* — Adrienne C. Love (57) ABSTRACT

A combination apparatus integrates the operation of a snorkel with a diving regulator having a breathing chamber and a diaphragm/purge valve chamber. A compressed air tank is in fluid communication with the diving regulator and a normally closed regulator valve is disposed between the compressed air tank and the diving regulator. A regulator valve spring maintains the regulator valve in the normally closed position. In a first embodiment, the regulator valve spring exerts about eight pounds per square inch on the normally closed regulator valve. Air enters into the breathing chamber from the compressed air tank through the diaphragm/purge valve chamber when the submerged diver inhales. The apparatus enables surface snorkeling and underwater diving and the diver need not switch from a snorkel mouthpiece to a diving regulator mouthpiece. Further embodiments re-locate the snorkel tube exhaust valve and add a two-position valve to the snorkel main tube.

4 Claims, 11 Drawing Sheets

INTEGRATED DIVING SNORKEL AND REGULATOR AND METHODS OF USE

BACKGROUND OF THE INVENTION

1. Field of the Invention

This invention relates, generally, to an integrated snorkel and diving regulator for use while snorkeling near a water surface and while diving under water. It also relates to structure for reducing the pressure of a high-pressure gas to a breathable pressure.

2. Description of the Prior Art

SCUBA (Self-Contained Underwater Breathing Apparatus) divers typically use a conventional snorkel to preserve air from the SCUBA air supply pressurized tank when swimming on or near the surface, i.e., at snorkeling depth, and viewing under water. When a diver decides to dive below the water surface, the diver removes the snorkel tube mouthpiece, clears the SCUBA diving regulator with a blast of air from the pressurized tank, and commences breathing through the mouthpiece of the SCUBA diving regulator so that the diver can continue breathing pressure-regulated air from the tank while submerged.

There are several patents disclosing products on separate diving snorkels and diving regulators. None of these products have successfully integrated a snorkel with a diving regulator, enabling a diver to seamlessly transition from breathing atmospheric air when swimming at snorkeling depth to breathing pressure-regulated air from a tank when submerged.

Thus there is a need for an integrated diving snorkel/regulator that combines the operation of a snorkel with that of a diving regulator, enabling snorkeling and underwater diving using a single apparatus.

A conventional snorkel has a tubular main body. A mouthpiece is secured to a first or proximal end of the tubular main body and a valve is mounted to a second or distal end of the tubular main body. When the swimmer submerges, the valve closes, prohibiting water from entering the tubular main body. No air is supplied to the snorkeler during such submersion.

A conventional SCUBA diving regulator enables a diver to breathe air supplied from a pressurized tank strapped to the diver's back. Pressure regulators perform the function of reducing the air pressure in the tank, usually in two stages, before it reaches the diver. The first stage is typically located at the SCUBA diving tank, and reduces the tank pressure to an intermediate pressure.

The second (demand) stage supplies air when the diver inhales and exhausts air when the diver exhales. The demand stage usually includes a mouthpiece, a piston or diaphragm that senses when the diver inhales, a breathing chamber that fills with air, an exhaust valve that vents exhaled air to the water, and a sensitivity adjustment means by which the diver can adjust the air flow from the first stage regulator. A conventional sensitivity adjustment means includes an elongate valve having a valve seat, a rocker arm, and a spring. A valve seat is seated in a volcano orifice when the first stage is closed.

Figure 1:
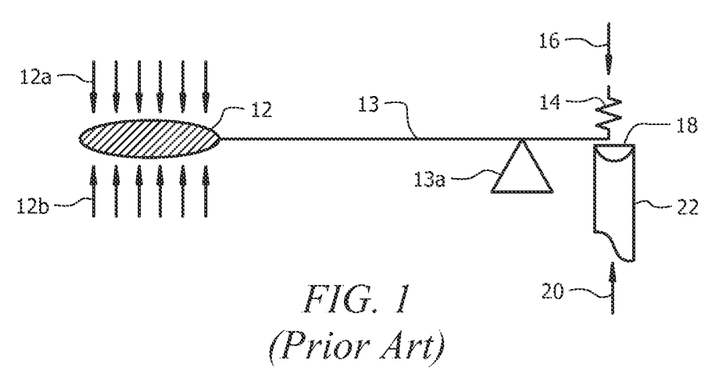
FIG. 1 schematically depicts a prior art diving regulator in its valve-closed, equilibrium configuration.

Conceptually, a conventional diving regulator employs a simple lever and fulcrum system as depicted in FIG. 1 (Prior Art).

Under normal operating conditions, air pressure within the breathing chamber of a diving regulator balances the water pressure acting on the outside of diaphragm 12. External water pressure acting on diaphragm 12 is indicated by directional arrows 12a and the air pressure inside the mouthpiece is indicated by directional arrows 12b.

Diaphragm 12 and valve spring 14 are connected to one another by lever 13 which pivots about fulcrum 13a when the competing pressures represented by directional arrows 12a and 12b are not in balance. FIG. 1 depicts the equilibrium position of lever 13 when said pressures are balanced.

The bias of regulator valve spring 14 provides a closing force indicated by directional arrow 16 that is applied to regulator valve 18 to contain tank pressure indicated by directional arrow 20 and to ensure that regulator valve 18 remains closed under slight variations of water or tank pressure. Regulator valve 18 is in fluid communication with tank pressure 20 through air inlet hose 22. Regulator valve 18 is closed as depicted when lever 13 is in its position of equilibrium or repose.

Typically, the compressed air tank provides a pressure of one hundred twenty to one hundred fifty pounds per square inch (120-150 psi), and the area of regulator valve 18 is about three-hundredths square inches (0.03 in$^2$). This requires a valve spring bias force 16 of about four to five pounds (4-5 lbs).

Figure 2:
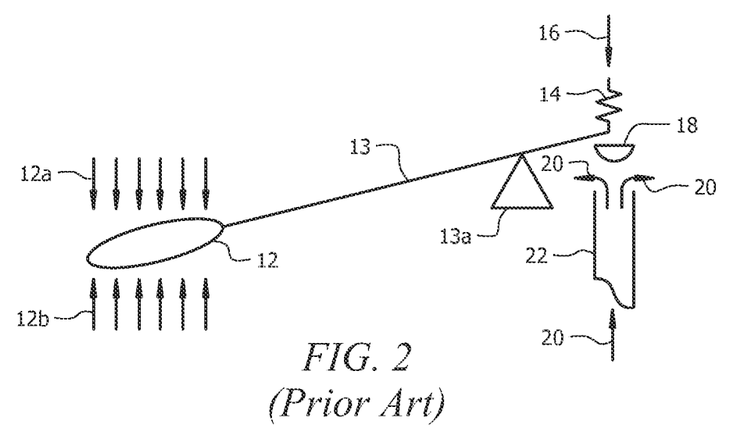
FIG. 2 schematically depicts the prior art diving regulator of FIG. 1 in its valve-open, non-equilibrium configuration.

As depicted in FIG. 2 (Prior Art), when a diver submerges, external water pressure 12a increases, causing lever 13 to pivot about fulcrum 13a, thereby overcoming the bias 16 of valve spring 14 and enabling the opening of regulator valve 18. When regulator valve 18 opens, air 20 from the diving tank enters into the breathing chamber, not depicted in FIG. 2. This equalizes pressures 12a and 12b. Lever 13 returns to its FIG. 1 position of repose and regulator valve 18 returns to its closed position under bias 16 of valve spring 14.

A similar situation occurs when the diver breathes from the diving regulator mouthpiece. The air pressure within the breathing chamber is reduced by an inhalation, causing lever 13 to pivot about fulcrum 13a, opening regulator valve 18. This allows air from the compressed air tank to fill the breathing chamber, pass through the mouthpiece and enter into the diver's lungs. When the diver has finished taking a breath, air 20 from the tank once again causes pressure 12b within the breathing chamber to balance or equalize with external water pressure 12a.

The interconnection of a conventional snorkel to a conventional diving regulator results in an imbalance between water pressure 12a with air pressure 12b within the breathing chamber of the diving regulator. When the diver is on or near the surface of the water, i.e., swimming at snorkeling depth, the distal end of the snorkel is in open fluid communication with the atmosphere. Therefore, the air pressure within the diving regulator breathing chamber is also at atmospheric pressure, i.e., nominally 14.7 psi). The pressure of the water, however, increases at a rate of thirty six hundredths pounds per square inch per inch (0.036 psi per inch) of depth. At typical snorkeling depths of eight to twelve inches (8-12"), water pressure 12a acting on the outside of diaphragm 12 is about fifteen and one-tenth pounds per square inch (15.1 psi), resulting in a pressure differential relative to atmospheric pressure of about four-tenths of a pound per square inch (0.4 psi).

An imbalance between said water pressure 12a with air pressure 12b within the breathing chamber causes lever 13 to pivot about fulcrum 13a and to open regulator valve 18, causing air to flow from the diving tank into the breathing chamber as aforesaid. However, due to its open fluid communication with the snorkel, the distal end of which is not submerged, the diving regulator breathing chamber is open to the atmosphere and air pressures 12a and 12b cannot balance one another. This is known as a free flow condition, i.e., regulator valve 18 does not close and air 20 from the diving tank continues to vent to the atmosphere.

For this reason, the known combinations of snorkels and diving regulators waste the air in the SCUBA tank during snorkeling.

It would be desirable to combine the functions performed by a snorkel and a SCUBA diving regulator. However, these are two separate structures and the solution to the free flow condition was not obvious to those of ordinary skill, in view of the prior art as a whole, at the time the invention was made.

SUMMARY OF THE INVENTION

The long-standing but heretofore unfulfilled need for a combined snorkel and SCUBA diving regulator that is not subject to the free flow condition where the diving regulator valve remains open at all times during snorkeling so that air within the SCUBA tank continuously and wastefully vents to the atmosphere, is now met by a new, useful, and non-obvious invention.

The novel apparatus has utility in SCUBA applications, where it replaces the conventional diving snorkel and SCUBA diving regulator.

The novel snorkel is attached to a SCUBA diving regulator. When the diver is swimming on or near the surface of the water, the distal end of the snorkel tube is above water, and the diver can inhale air from the atmosphere through the snorkel tube. The regulator valve of the diving regulator is closed, thereby preventing the free flow condition. When the diver submerges, the snorkel tube is automatically or manually closed, and the air supply is automatically switched to pressure-regulated air from a SCUBA diving tank. The novel structure prevents the free-flow phenomenon and therefore prevents wasting the air in the SCUBA tank during snorkeling.

The novel apparatus and method are further advantageous because the diver need not remove a snorkel mouthpiece and replace it with the mouthpiece from a SCUBA diving regulator when transitioning from surface swimming to under water swimming.

In all embodiments, the snorkel includes a snorkel tube and the diving regulator includes a breathing chamber. The snorkel tube is in fluid communication with the breathing chamber. The diving regulator includes a diaphragm/purge valve chamber in fluid communication with the breathing chamber and a diving regulator mouthpiece in fluid communication with the breathing chamber. The diving regulator mouthpiece is adapted to be used by a diver when swimming at snorkeling depth or when diving below the water surface. The diver manually presses on the diaphragm to purge air from the system when preparing to dive. Pressing on the diaphragm opens the regulator valve.

A novel regulator valve spring maintains the normally closed regulator valve in the normally closed position. The regulator valve spring exerts about eight pounds per square inch on the normally closed regulator valve so that compressed air in the compressed air tank cannot escape into the atmosphere through the snorkel because the bias exerted by the novel regulator valve spring prevents the regulator valve spring from opening when an unsubmerged snorkel-user inhales.

A first embodiment of the combination apparatus that integrates the operation of a snorkel and a diving regulator includes a compressed air tank, a diving regulator in fluid communication with the compressed air tank, and a normally closed regulator valve disposed between the compressed air tank and the diving regulator.

A normally-closed exhaust valve is positioned at a distal end of the snorkel tube. A bias means holds the exhaust valve in the normally closed position so that the exhaust valve opens only when the user is exhaling and closes at the end of any exhalation.

A slideably mounted snorkel float valve is positioned near the distal end of the snorkel tube. At least one air hole is formed in the snorkel tube between the exhaust valve and the snorkel float valve. The exhaust valve, snorkel float valve, and air holes are above a water surface when the user is swimming on or near the water surface. The snorkel float valve closes the air holes when the user submerges, thereby sealing the snorkel tube and the breathing chamber from water.

Air enters into the breathing chamber from the compressed air tank through the regulator valve when the submerged diver inhales. Breathing is laborious, however, since the diver must draw sufficient vacuum to overcome the higher force of the regulator valve spring.

The apparatus enables snorkeling and underwater diving in the absence of a requirement for the diver to switch from a snorkel mouthpiece to the diving regulator mouthpiece.

A second embodiment does not employ the eight pound spring of the first embodiment. Instead, it adds a four pound auxiliary spring in series with the conventional four pound spring to supply a total bias of eight pounds to hold the regulator valve closed.

Compressed air in the compressed air tank cannot escape into the atmosphere through the snorkel because the combined force of a conventional regulator valve spring plus the auxiliary spring is sufficient to overcome the pressure differential between the water pressure acting on the diaphragm at the snorkeling depth or 8-12 inches (15.1 psi), and atmospheric pressure, since the snorkel is open to the atmosphere (14.7 psi). When the snorkeler inhales, the pressure drop (14.7 psi) is negligible, because the end of the snorkel is open to the atmosphere.

There are multiple ways to implement the auxiliary regulator spring. For example, the auxiliary spring may be engaged either manually or automatically when the diver transitions from snorkeling to diving. The auxiliary tension spring may act on the diaphragm that is engaged by turning the valve that closes the snorkel. The auxiliary spring may be provided in the form of an elastic band, a conventional metallic spring, or other suitable bias means.

The auxiliary spring is preferably attached to a fulcrum-mounted lever that abuttingly engages the diaphragm. More particularly, a first end of the lever is connected to the diaphragm and a second end of the lever is connected to the regulator valve spring. The lever and fulcrum provide a mechanical advantage that reduces the amount of force that must be applied to the second end of the lever to produce the effect of an additional four pounds per square inch applied to the normally closed regulator valve.

The force of the auxiliary spring may be adjusted by changing its anchor point on a turning mechanism by means of a spline joint, changing its stiffness by changing its material type or cross sectional area, or by increasing or decreasing its preload by changing the amount of rotation of the turning mechanism.

The diver disconnects, disengages, or reduces the auxiliary regulator valve spring force to zero when submerging so that air enters into the breathing chamber from the compressed air tank through the diaphragm/purge valve chamber when the submerged diver inhales. Thus, removal of the novel auxiliary valve spring force upon submersion returns the apparatus to its conventional configuration.

A third embodiment that also prevents occurrence of the free-flow phenomenon is simpler than the auxiliary spring embodiment in that it includes no auxiliary spring. A fixed outer tube has three apertures formed in it, a first aperture providing fluid communication with a snorkel breathing tube, a second aperture providing fluid communication with a regulator breathing chamber, and a third aperture providing fluid communication with a mouthpiece. The first aperture is formed near an open end of the tube and the second and third apertures are formed near a closed end of the tube.

The first and second apertures are longitudinally aligned with one another and are pointed upward when in use, i.e., the rotational position of the tube is selected so that the axis of symmetry of each aperture is perpendicular or approximately perpendicular to a water surface when the tube is submerged. The third aperture is circumferentially spaced apart from the second aperture by ninety degrees (90°), i.e., the axis of symmetry of the third aperture is parallel or approximately parallel to the surface of the water when the respective axes of symmetry of the first and second apertures are perpendicular or approximately perpendicular to the water surface.

An inner tube having three apertures formed therein is positioned within the lumen of the outer tube in concentric relation thereto. The inner tube is mounted for ninety degree (90°) axial rotation relative to the outer tube.

A first inner tube aperture is in alignment with the first aperture formed in the outer tube. A second inner tube aperture is in alignment with the third, mouthpiece aperture of the outer tube. A third inner tube aperture is circumferentially spaced from the second outer tube aperture by one hundred eighty degrees (180°) and is therefore circumferentially spaced from the mouthpiece aperture of the outer tube by ninety degrees (90°).

A knob adapted to be rotated by a user is secured to a first end of the inner tube, said knob closing said first end. The second end of the inner tube is closed as is the second end of the outer tube. The outer tube is non-rotatably mounted so that rotation of the inner tube has no effect on the outer tube.

When the novel apparatus is used for snorkeling, the outer tube first aperture is in alignment with the inner tube first aperture and both apertures are therefore in fluid communication with the snorkel tube. Moreover, the mouthpiece aperture of the outer tube is in alignment with the mouthpiece aperture of the inner tube. The second aperture of the outer tube is blocked by an imperforate extent of the inner tube. The third aperture of the inner tube is blocked by an imperforate extent of the outer tube. This rotational alignment of the outer and inner tubes enables a user to breathe air directly through the snorkel tube when at snorkeling depth.

When below snorkeling depth, the user rotates the inner tube ninety degrees (90°) so that the first (snorkel tube) aperture formed in the inner tube is blocked by an imperforate extent of the outer tube. The second (mouthpiece) aperture of the inner tube is thereby rotated ninety degrees (90°) into alignment with the second aperture formed in the outer tube, which second aperture is in open fluid communication with a diving regulator breathing chamber. This rotation brings the third aperture of the inner tube into alignment with the third (mouthpiece) aperture of the outer tube, thereby enabling the diver to breathe directly from said regulator breathing chamber.

This third embodiment avoids the need for an auxiliary spring and provides a simplified, intuitive method for switching from a snorkeling mode to a diving mode, i.e., it requires just a simple rotation of a tube. The apertures need not be round or oval, i.e., they may have any functional shape that can be effectively sealed, including square.

A fourth embodiment of the novel combination apparatus includes a compressed air tank, a snorkel tube, and an imperforate cap that closes a distal free end of the snorkel tube, i.e., the normally closed exhaust valve of the first and second embodiments is replaced with a permanently closed imperforate cap. The normally closed exhaust valve is re-located to the diving regulator. The imperforate cap, snorkel float valve, and air holes are above a water surface when a user is swimming at snorkeling depth.

The diving regulator includes a breathing chamber. A proximal end of the snorkel tube is in fluid communication with the breathing chamber. The diving regulator includes a diaphragm/purge valve chamber in fluid communication with the breathing chamber. The diaphragm/purge valve chamber housing includes a diaphragm and a purge valve. A purge valve actuator actuates the purge valve.

A normally closed regulator valve is disposed between a breathing chamber inlet and the compressed air tank. A diving regulator mouthpiece is in fluid communication with the breathing chamber. The normally closed exhaust valve is mounted on the diving regulator in fluid communication with the breathing chamber.

The exhaust valve is biased into a normally closed position so that it opens only when the user is exhaling and closes at the end of any exhalation. The snorkel float valve closes the air holes, thereby sealing the snorkel tube and the breathing chamber from water when the diver submerges. Exhaled air is exhausted from the breathing chamber through the exhaust valve when the diver is submerged. Accordingly, pressure within the breathing chamber is reduced when the user inhales. The regulator valve opens when the user inhales, allowing air to enter the breathing chamber at the inlet.

A fifth embodiment incorporates a two-position valve disposed in the snorkel tube between the snorkel tube air holes and the breathing chamber to prevent water from entering into the breathing chamber and to prevent air from leaking out of the snorkel tube. The two-position valve is open when a diver is swimming at snorkeling depth and breathing ambient air through the snorkel tube and is closed when the diver is submerged.

When closed, the two-position valve seals the breathing chamber from air and water so that the diver can breathe air from the pressurized air tank and so that exhaled air flows through the exhaust valve mounted on the diving regulator in fluid communication with the breathing chamber. The diver opens the two-position valve and purges the combination apparatus with air by blocking the mouthpiece and pressing on the purge valve actuator of the diaphragm/purge valve chamber, thereby expelling water from the breathing chamber and the snorkel tube. When the two-position valve is closed, the snorkel float valve is not required and may be removed. If not removed, the snorkel tube could be crushed by water pressure on deep dives. If removed, pressure acting on the snorkel tube is equalized inside and out, thereby maintaining the structural integrity of the snorkel tube even when the tube is deeply submerged. Most diving is no more than twenty five feet in depth and water pressure at that depth is not sufficient to crush a conventional snorkel tube so it is OK under those conditions to leave the conventional snorkel float valve in place when the two-position valve is closed.

The regulator valve has an internal bias which maintains it in a normally closed configuration so that air flows from the ambient atmosphere through the snorkel air holes into the breathing chamber when the diver inhales while snorkeling. The air holes are closed by the float valve when the diver submerges. The re-located exhaust valve, i.e., the exhaust valve mounted on the diving regulator, opens when the submerged diver exhales because the exhaled air cannot flow through the closed two-position valve and the pressure of the exhaled air is sufficient to overcome the bias of the spring that holds the re-located exhaust valve normally closed.

The regulator valve is open when the diver inhales because inhaled air cannot flow through the closed two-position valve so the suction created by an inhalation overcomes the bias of the regulator valve spring that holds the regulator valve closed and inhaled air flows into the breathing chamber from the compressed air tank through an air hose.

The two-position valve may be opened and closed manually by the diver or by an automatic float device.

A sixth embodiment includes a piston slideably mounted in a cylinder. When the piston is in a first position, air from the snorkel tube is blocked and the mouthpiece is in open fluid communication with a compressed air tank through the diving regulator valve. When the piston is in a second position, air from the compressed air tank is blocked and the mouthpiece is in open fluid communication with the snorkel tube. The user moves the piston to the desired position by pushing or pulling on a handle which is connected to the piston.

A seventh embodiment includes a rotatably mounted valve. When in a first position, the valve blocks air flow from a compressed air tank and permits inhaled airflow from the snorkel tube to the mouthpiece and exhaled airflow from the mouthpiece to the snorkel tube. When in a second position, the valve blocks airflow from the snorkel tube and permits inhaled airflow from a compressed air tank through the diving regulator valve to the mouthpiece and exhaled air flow from the mouthpiece to an exhaust valve mounted on the diving regulator.

An eighth embodiment includes a valve that performs two (2) functions simultaneously. In a first position, it cuts off airflow from the snorkel and engages (FIG. 4 embodiment) or disengages (FIG. 5 embodiment) the auxiliary spring of the second embodiment so that the user may dive below snorkeling depth. In a second position, it opens the snorkel and engages the auxiliary spring so that the user can swim at snorkeling depth with no free flow.

An important object of this invention is to provide a combination snorkel and SCUBA apparatus that is not subject to the free-flow phenomenon.

Another important object is to provide a combination snorkel and SCUBA apparatus that does not require a diver to remove a snorkel mouthpiece and replace it with the mouthpiece from a SCUBA diving regulator when transitioning from snorkeling to diving.

Another object is to enable a user to easily and quickly switch from one mode to another, either from snorkeling to diving or from diving to snorkeling.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

Figure 3:
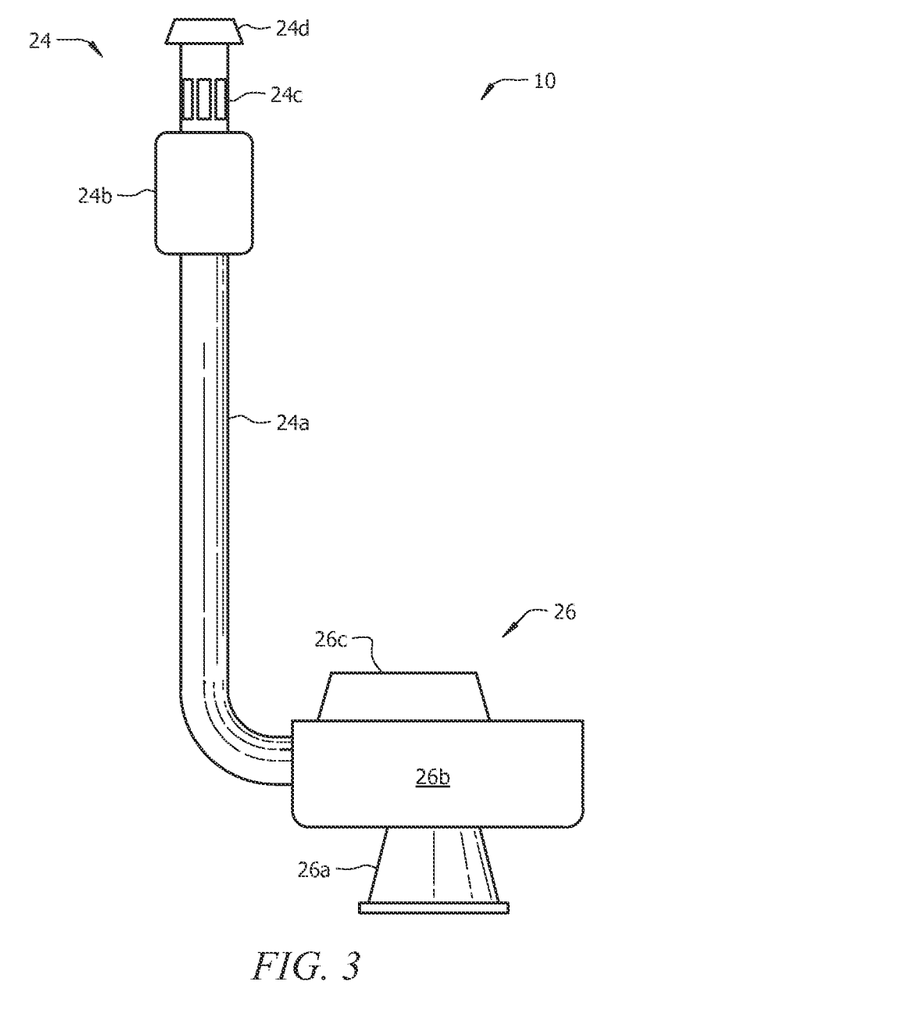
FIG. 3 is a side elevational view of a first embodiment of the novel structure.

FIG. 3 depicts an illustrative first embodiment of the invention, denoted 10 as a whole. Novel structure 10 integrates the operation of a conventional snorkel 24 with novel diving regulator 26, enabling snorkeling and diving using a single apparatus.

In FIG. 3, the exhaust port 24d surmounts snorkel tube 24a. This position is advantageous for diving underwater as the bubbles from exhaust port 24d are spaced away from the diver and not within the diver's field of view. This position of exhaust port 24d is disadvantageous to the extent that it requires connection of snorkel 24 to diving regulator 26 even when the snorkel is not needed.

Conventional snorkel 24 includes snorkel tube 24a, float valve 24b, air holes 24c and exhaust valve 24d. Exhaust valve 24d is positioned at the distal end of snorkel tube 24a and slideably mounted snorkel float valve 24b is positioned near said distal end as depicted. When a user is swimming at snorkeling depth, i.e., on or near the surface of the water, exhaust valve 24d, snorkel float valve 24b, and air holes 24c therebetween are above the water surface. The user breathes ambient air through air holes 24c. Air from a SCUBA tank, not depicted in FIG. 3, is not expended because the strength of the regulator valve bias spring is sufficient to resist the pressure differential from the water (15.1 psi) and air pressure (14.7 psi).

Exhaust valve 24d is biased into a normally closed position so that it opens only when a user is exhaling. When the diver submerges, exhaust valve 24d closes at the end of any exhalation that follows such submersion, and float valve 24b closes air holes 24c, sealing snorkel tube 24a and breathing chamber 26b from water.

Diving regulator 26 is not conventional but as depicted it includes conventional mouthpiece 26a, breathing chamber 26b and housing 26c that includes diaphragm 12 and a purge valve.

Snorkel tube 24a is in fluid communication with diving regulator mouthpiece 26a, breathing chamber 26b, and diaphragm/purge valve chamber 26c.

Diving regulator 26 is not conventional because in this first embodiment, regulator valve spring 14 of the prior art is replaced by a valve spring having an increased stiffness, i.e., said stiffness being a constant k in the equation that expresses Hooke's law, $F=kx$, where the force F required to lengthen or shorten a spring by distance x is directly proportional to that distance.

A conventional diaphragm 12 has a surface area of about two square inches ($2\ in^2$), resulting in a net force imbalance of eight-tenths of a pound (0.8 lbs) acting on the diaphragm when the diver is swimming at snorkeling depth. The mechanical advantage of lever 13 in prior art FIG. 1 is typically ten-to-one (10:1).

The novel regulator valve spring is not independently depicted in FIG. 3 because it has the same appearance and position as its prior art counterpart, regulator valve spring 14. The novel regulator valve spring of tis first embodiment differs from conventional regulator valve spring 14 because said novel valve spring provides a force of about eight pounds per square inch (8 lbs psi) to keep conventional regulator valve 18 closed when the diver is at snorkeling depth. Conventional regulator valve spring 14 provides a force of about four to five pounds (4-5 lbs) to keep regulator valve 18 closed. The novel spring thus provides an additional four pounds (4 lbs) of force. This eliminates the "free flow" condition.

This first embodiment works best when the diver is swimming at snorkeling depth. When a diver is below snorkeling depth with snorkel float valve 24b in its air hole-closing position, breathing through the novel, stiffening-enhanced regulator valve spring is difficult because the diver must inhale with increased effort to sufficiently reduce the pressure in the breathing chamber to enable the regulator valve to open.

In a second embodiment, conventional regulator valve spring 14 is not replaced but is augmented by a second, auxiliary spring that has the effect of increasing the stiffness of conventional regulator valve spring 14 when the user is snorkeling, or reducing the stiffness of the regulator valve spring when the user is diving.

In the first embodiment, the stiffness of regulator spring 14 is increased when the diver is at the surface of the water. Below the surface, the auxiliary spring pulls on the end of lever 13 to off-load said regulator spring 14. In this second embodiment, the stiffness of regulator spring 14 is increased by adding another spring in series with spring 14, or using an elongate regulator spring that can be screwed in and out to increase or decrease its stiffness. The first two embodiments of this invention thus perform the same function by different means.

An apparatus having a stiff regulator valve spring that eliminates free flow while snorkeling and a weak regulator spring while diving to make breathing easier would be ideal. The second embodiment of this invention includes two structurally distinct variations that provide such ideal functionality.

Figure 4:
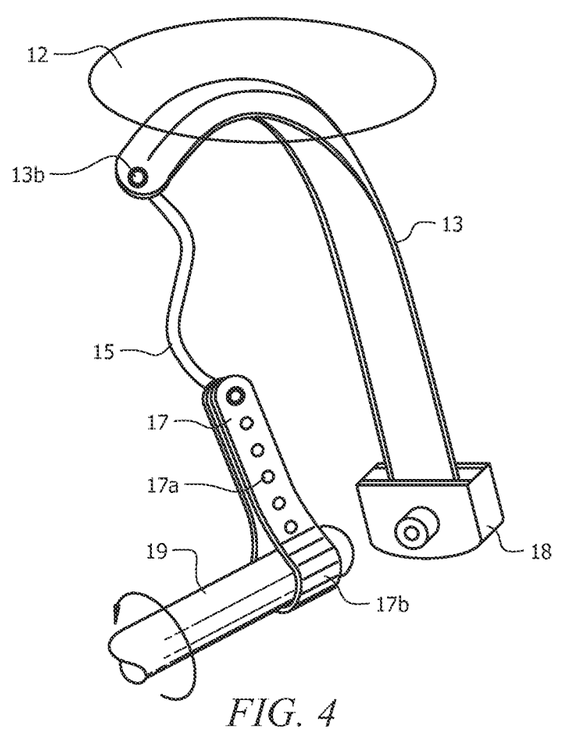
FIG. 4 is a diagrammatic perspective view of an auxiliary tension spring that adjusts the force applied by a regulator valve spring in connection with a second embodiment.

In a first variation, depicted in FIG. 4, a stiff regulator valve spring is employed and a means is provided for off-loading the spring when the diver is under water. Such means, in effect, provides a stiff spring when snorkeling and a weaker spring when diving, i.e., the stiff auxiliary regulator valve spring of the FIG. 4 embodiment is engaged when the user is at diving depth.

Figure 5:
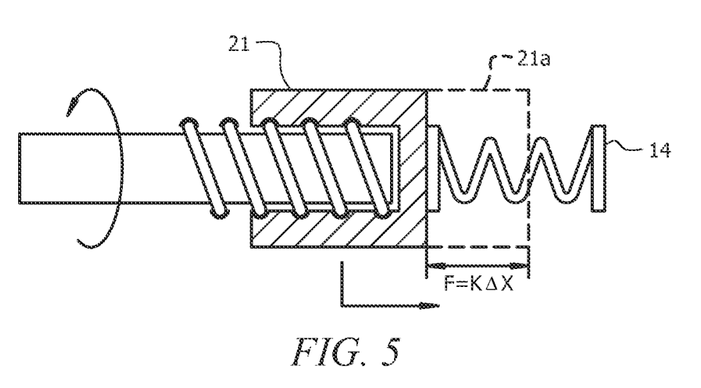
FIG. 5 is a diagrammatic side elevational view of an auxiliary compression spring that adjusts the force applied by a regulator valve spring in connection with the second embodiment.

In the second variation, depicted in FIG. 5, a weak auxiliary regulator valve spring is employed when the user is diving and its stiffness is augmented, i.e., increased to eliminate free flow when the user is snorkeling. Thus, the relatively weaker auxiliary regulator valve spring is disengaged when the user is at diving depth.

More particularly, when a conventional regulator valve spring 14 is used, a compression auxiliary spring is applied directly to said conventional regulator valve spring, or to the diaphragm. A stiffer compression spring, i.e., one applying about four pounds of force, is necessary if it is applied directly to regulator valve spring 14. Since the lever/fulcrum assembly provides about a 10:1 mechanical advantage, only 0.4 lbs is needed if the auxiliary spring is applied to the diaphragm.

When a valve regulator spring has a stiffness higher than that of a conventional regulator valve spring, a tension auxiliary spring can be applied directly to the diaphragm. This reduces the apparent stiffness of the valve regulator spring. Alternately, a mechanism can be provided that reduces the pre-load in the valve regulator spring having enhanced stiffness.

The auxiliary spring may be positioned at either end of lever 13 to enhance the closing force on regulator valve 18. The diver manually engages the novel auxiliary spring while swimming at snorkeling depth using snorkel 24 and disengages the novel auxiliary spring when below snorkeling depth. However, the auxiliary spring could be automatically engaged or disengaged, depending upon the embodiment in use, by a mechanism that would sense when snorkel float valve 24b rises and closes air holes 24c, indicating that the diver has submerged. For example, the rising of the float valve could be electronically sensed and cause generation of a signal to engage or disengage the auxiliary spring, depending upon the embodiment in use as mentioned above in connection with the embodiments of FIGS. 4 and 5.

When the auxiliary spring is engaged, its strength is added to the strength of conventional regulator valve spring 14, thereby preventing free flow when the diver is snorkeling. This second embodiment improves upon the single spring first embodiment because the auxiliary spring is released after submersion below snorkeling depth and the diver is therefore not subjected to the above-mentioned difficulty caused by the strong single spring of the first embodiment.

The auxiliary spring of the second embodiment may take the form of a tension spring as depicted in FIG. 4. Lever 13 in this embodiment is formed of a flexible material having a bend formed therein and has a first end secured to regulator valve 18 and a distal free end having aperture 13b formed therein. The bight of the bend bears against diaphragm 12.

Elastomeric cord 15 or other flexible bias means such as a coil spring has a first end that engages aperture 13b and a second end that engages a preselected aperture 17a of a plurality of apertures, collectively denoted 17a, formed in anchor arm 17. Anchor arm 17 has an internally splined cylindrical base 17b that receives shaft 19 that is externally splined at its leading end to engage the internal splines formed in cylindrical base 17b. Anchor arm 17 extends radially outwardly with respect to an axis of symmetry of said cylindrical base in perpendicular relation to said axis of symmetry. Rotation of shaft 19 effects simultaneous and corresponding rotation of anchor arm 17 about said axis of symmetry. Such rotation causes elastic cord 15 to become taut and to pull on the distal free end of lever 13 at point 13a. The length and the elasticity of cord 15 thus determine the amount of force applied to diaphragm 12 by said bight of said lever 13.

The lever 13/fulcrum 13a apparatus provides a mechanical advantage that enables elastic cord 15 or other suitable tensioning means to have a lighter structure and a lower bias.

The force exerted by regulator valve spring 14 may also be varied by the structure depicted in FIG. 5 which includes no elastic band and no anchor arm. An internally threaded cylindrical cap 21 screwthreadedly receives an externally threaded variation of shaft 19. Rotation of shaft 19 in a first rotational direction effects travel in a first axial direction of the leading end of cap 21 that abuts regulator valve spring 14 and causes increased compression of spring 14. Rotation of shaft 19 in a second rotational direction opposite to the first rotational direction effects axial travel in a second axial direction opposite to said first axial direction of the leading end of cap 21 and causes decreased compression of spring 14. The range of travel of cap 21 is depicted in dotted lines and denoted 21a.

This second embodiment also eliminates "free flow" when snorkel 24 is used at or near the surface of the water This second embodiment allows normal, unimpeded breathing when the diver is below snorkeling depth when the auxiliary spring is disengaged. When the submerged diver inhales, air enters into breathing chamber 26b from a compressed air tank through regulator valve 18. This embodiment relies on the airtight and watertight sealing of snorkel float valve 24b, and is advantageous because it vents exhaust air away from the diver, thereby minimizing bubbles within a submerged diver's field of view. It is disadvantageous because snorkel tube 24a is subject to being crushed at significant depths.

Figure 6A:
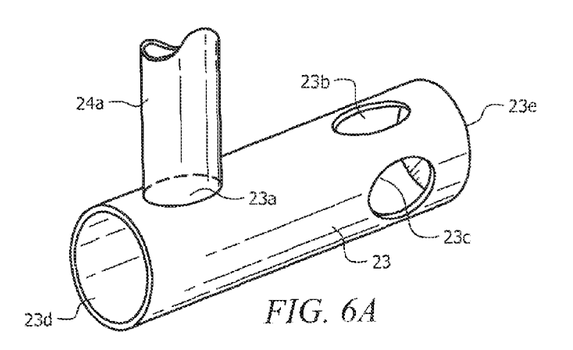
FIG. 6A is a perspective view of an outer tube employed in a third embodiment.
Figure 6B:
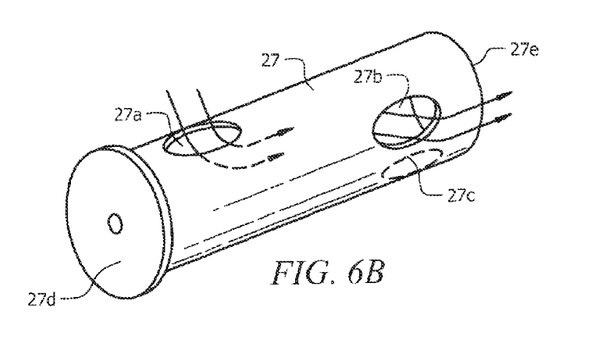
FIG. 6B is a perspective view of an inner tube employed in the third embodiment.
Figure 6C:
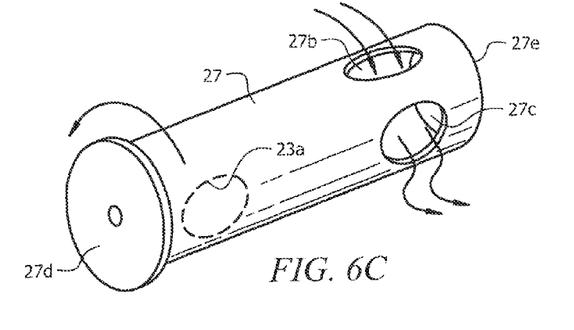
FIG. 6C is a perspective view depicting the inner tube and the outer tube when the apparatus of the third embodiment is configured for diving.

FIGS. 6A-6C depict a third embodiment that also prevents occurrence of the free-flow phenomenon. It differs from the auxiliary spring embodiment in that it includes no auxiliary spring. A fixed outer tube 23 has three apertures formed in it, a first aperture 23a providing fluid communication with a snorkel breathing tube, a second aperture 23b providing fluid communication with a regulator breathing chamber, and a third aperture 23c providing fluid communication with a mouthpiece. First aperture 23a, hereinafter referred to as the snorkel aperture of the outer tube, is formed near open end 23d of outer tube 23. The second and third apertures, hereinafter referred to as the regulator and mouthpiece apertures, respectively, are formed near closed end 23e of outer tube 23.

Snorkel and regulator apertures 23a, 23b are longitudinally aligned with one another and their respective axes of symmetry are pointed upward when in use, i.e., the rotational position of outer tube 23 is selected so that the axis of symmetry of each aperture 23a, 23b is perpendicular or approximately perpendicular to a water surface when the tube is submerged. Mouthpiece aperture 23c is circumferentially spaced apart from regulator aperture 23b by ninety degrees (90°), i.e., the axis of symmetry of mouthpiece aperture 23c is parallel or approximately parallel to the surface of the water when the respective axes of symmetry of snorkel and regulator apertures 23a, 23b are perpendicular or approximately perpendicular to the water surface.

Inner tube 27 having three apertures formed therein is positioned within the lumen of outer tube 23 in concentric relation thereto Inner tube 27 is mounted for ninety degree (90°) axial rotation relative to outer tube 23.

First inner tube aperture 27a, hereinafter referred to as snorkel aperture 27a of inner tube 27, is in alignment with snorkel aperture 23a formed in outer tube 23 when said outer and inner tubes are in a first position of rotational adjustment.

Second inner tube aperture 27b, hereinafter referred to as mouthpiece aperture 27b of inner tube 27, is in alignment with mouthpiece aperture 23c of outer tube 23 when said outer and inner tubes are in said first position of rotational adjustment.

Third inner tube aperture 27c, hereinafter referred to as regulator aperture 27c of inner tune 27, is circumferentially spaced from regulator aperture 23c by one hundred eighty degrees (180°) and is therefore circumferentially spaced from mouthpiece aperture 23b of outer tube 23 by ninety degrees (90°) when said outer and inner tubes are in said first position of rotational adjustment.

Knob 27d, adapted to be rotated by a user, is secured to first end 27e of inner tube 27, said knob closing said first end. Second end 27f of inner tube 27 is closed as is second end 23e of outer tube 23. Outer tube 23 is non-rotatably mounted so that rotation of inner tube 27 has no effect on outer tube 23.

When novel apparatus 10 is used for snorkeling, outer tube snorkeling aperture 23a is in alignment with inner tube snorkeling aperture 27a and both apertures are therefore in fluid communication with snorkel tube 24a. Moreover, mouthpiece aperture 23c of outer tube 23 is in alignment with mouthpiece aperture 27b of inner tube 27. Regulator aperture 23b of outer tube 23 is blocked by an imperforate extent of inner tube 27. Third aperture 27c of inner tube 27 is blocked by an imperforate extent of outer tube 23. This rotational alignment of the outer and inner tubes enables a user to breathe air directly through the snorkel tube when at snorkeling depth.

When below snorkeling depth, the user rotates the inner tube ninety degrees (90°) so that the first (snorkel tube) aperture formed in the inner tube is blocked by an imperforate extent of the outer tube as depicted in FIG. 6C. Mouthpiece aperture 27b of inner tube 27 is thereby rotated ninety degrees (90°) into alignment with regulator aperture 23b formed in outer tube 23, which aperture 23b is in open fluid communication with diving regulator breathing chamber 26b. This rotation brings mouthpiece aperture 27c of inner tube 27 into alignment with the mouthpiece aperture 23c of outer tube 23, thereby enabling the diver to breathe directly from regulator breathing chamber 26b.

Figure 7:
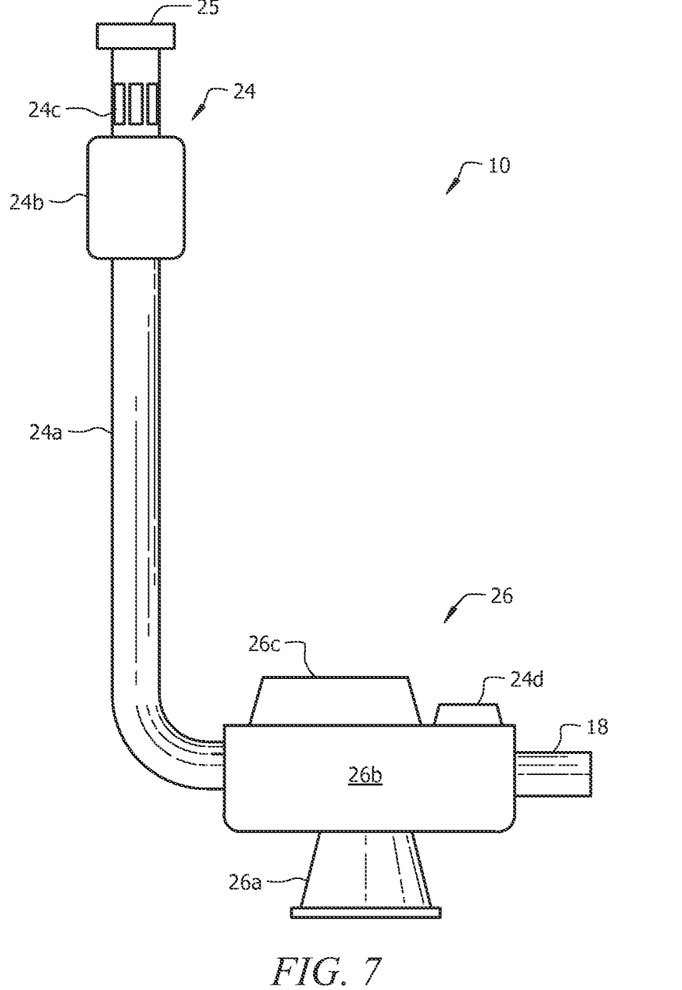
FIG. 7 is a side elevational view of a fourth embodiment of the novel structure.

FIG. 7 depicts a fourth embodiment where imperforate cap 25 replaces exhaust valve 24d at the distal free end of snorkel tube 24a so that no air can be exhaled through snorkel tube 24b. Snorkel exhaust valve 24d is re-located to diving regulator 26 where it is in valved communication with breathing chamber 26. This fourth embodiment is advantageous because the diver can remove the snorkel when it is not needed and plug the opening in the breathing chamber created by such detachment.

Cap 25 is an imperforate, permanently closed closure means. Float valve 24b closes air holes 24c in the conventional way when the diver submerges. Snorkel tube 24a and mouthpiece 26a are in fluid communication with breathing chamber 26b as in the first and second embodiments.

Accordingly, when a diver is swimming at snorkeling depth, inhaled and exhaled air flows through air holes 24c. When the diver submerges below snorkeling depth, float valve 24b closes air holes 24c, sealing snorkel tube 24a and breathing chamber 26b from water. When the diver exhales, air is exhausted from breathing chamber 26b through re-located exhaust valve 24d.

When the diver inhales, the pressure within breathing chamber 26b is reduced and regulator valve 18 in breathing chamber 26b opens, allowing air to enter said breathing chamber 26b through said open regulator valve 18 which is in valved fluid communication with a compressed air tank, not depicted in FIG. 6.

This fourth embodiment, like the first three embodiments, relies on the airtight and watertight sealing of snorkel float valve 24b when the apparatus is used below snorkeling depth. However, since exhaust valve 24d is in fluid communication with breathing chamber 26b, and is closed when the diver is not exhaling, the diver can disconnect snorkel tube 24a from breathing chamber 26b and manually plug the resulting opening in breathing chamber 26b when the diver is submerged and not relying on snorkel 24 as an air source. This is the only advantage of positioning the exhaust port on breathing chamber 26b. The diver can remove the snorkel, plug the hole, and it will be identical to a conventional regulator. However, the regulator spring must be of conventional stiffness or the auxiliary spring must be engaged to reduce the force of a conventional spring.

Figure 8:
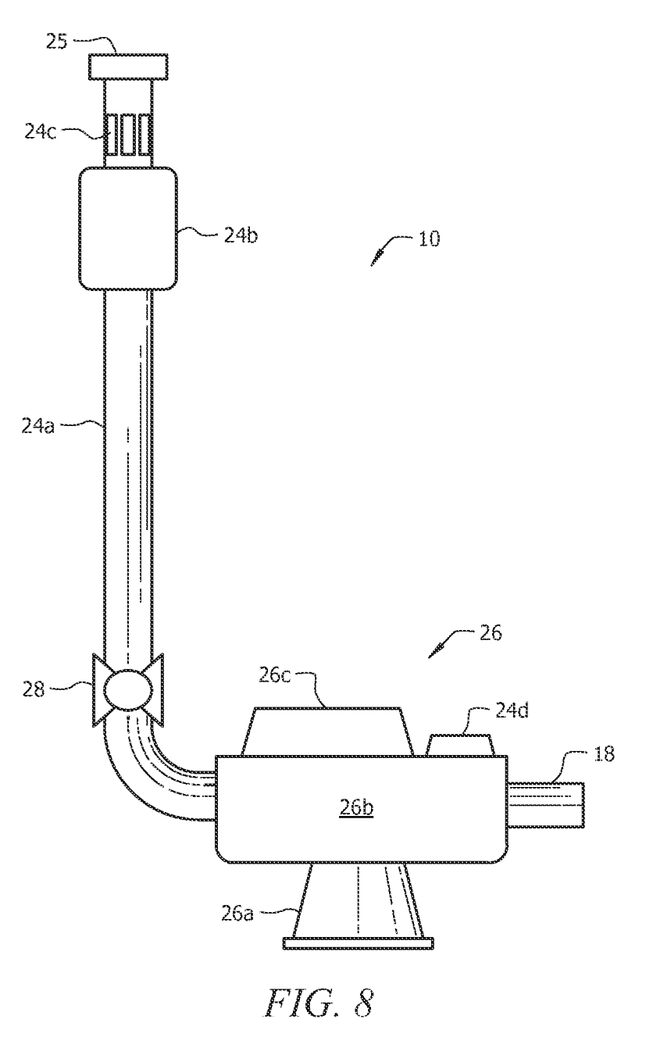
FIG. 8 is a side elevational view of a fifth embodiment of the novel structure.

FIG. 8 depicts a fifth embodiment which incorporates cap 25 and the re-location of exhaust valve 24d of the fourth embodiment and adds two-position valve 28 positioned between the free end of snorkel tube 24a and breathing chamber 26b to block water that may enter into breathing chamber 26b, and to block air that may leak out of snorkel tube 24a. Valve 28 may be opened and closed manually by the diver or it may be automatically opened and closed with a float or equivalent device.

Valve 28 is open when a diver is swimming at snorkeling depth and breathing ambient air through snorkel tube 24a. The strong spring of the first embodiment or the conventional spring enhanced with the force of the auxiliary spring of the second embodiment prevents free flow during such snorkeling. The diver closes valve 28 when the decision is made to submerge. When closed, valve 28 seals breathing chamber 26b from leaking air or water without relying upon float valve 24b. This enables the diver to breathe air from diving tank 30, and exhaust air through exhaust valve 24d.

This fifth embodiment does not require or rely upon snorkel float valve 24b as aforesaid, and more reliably prevents air and water leakage to or from breathing chamber 26b relative to the third embodiment. If snorkel float valve 24b is not used, snorkel tube 24a fills with water when the diver is below snorkeling depth. When the diver re-surfaces, the diver opens two-position valve 28 and purges the system with air by blocking mouthpiece 26a and pressing on the conventional purge valve actuator of diaphragm/purge valve chamber 26c, thereby expelling water from breathing chamber 26b and snorkel tube 24a.

This fifth embodiment also allows the diver to easily remove snorkel tube 24a if it is not needed. Sealing of breathing chamber 26b is accomplished by closing two-position valve 28 as aforesaid. If snorkel float valve 24b is not used, the pressure acting on snorkel tube 24a is equalized inside and out, thereby making snorkel tube 24a less prone to damage due to over-pressure when the diver is at significant depths.

Figure 9:
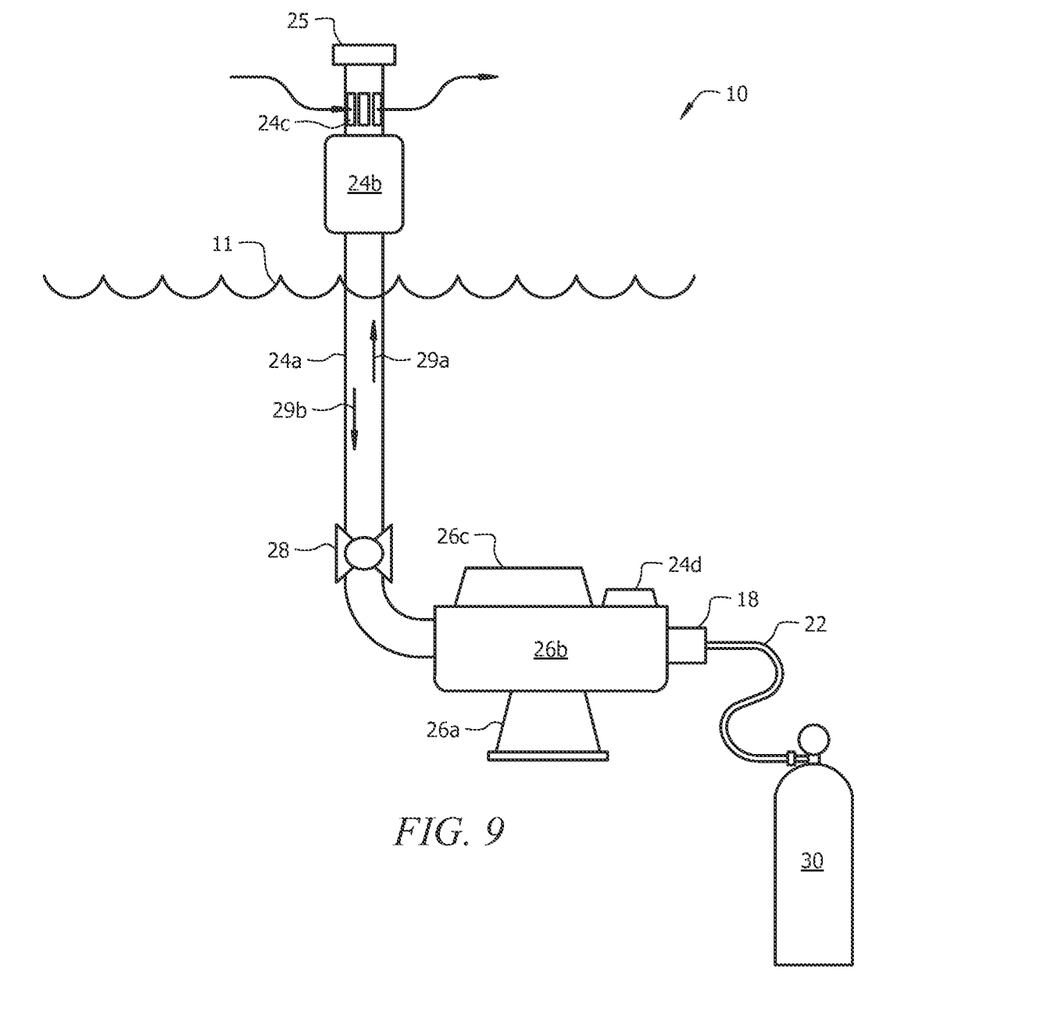
FIG. 9 is a side elevational view of a sixth embodiment.

FIG. 9 depicts the operation of the fifth embodiment of the novel structure when the diver is snorkeling at or near water surface 11 and valve 28 is open. Re-located exhaust valve 24d remains closed at all times because of an internal bias which maintains it in its normally closed position. Exhaled air follows the path of least resistance as indicated by directional arrow 29a when the diver exhales. Regulator valve 18 also remains closed for the same reason, i.e., inhaled air follows the path of least resistance as indicated by directional arrow 29b and no air flows from SCUBA tank 30 through air hose 22.

Figure 10:
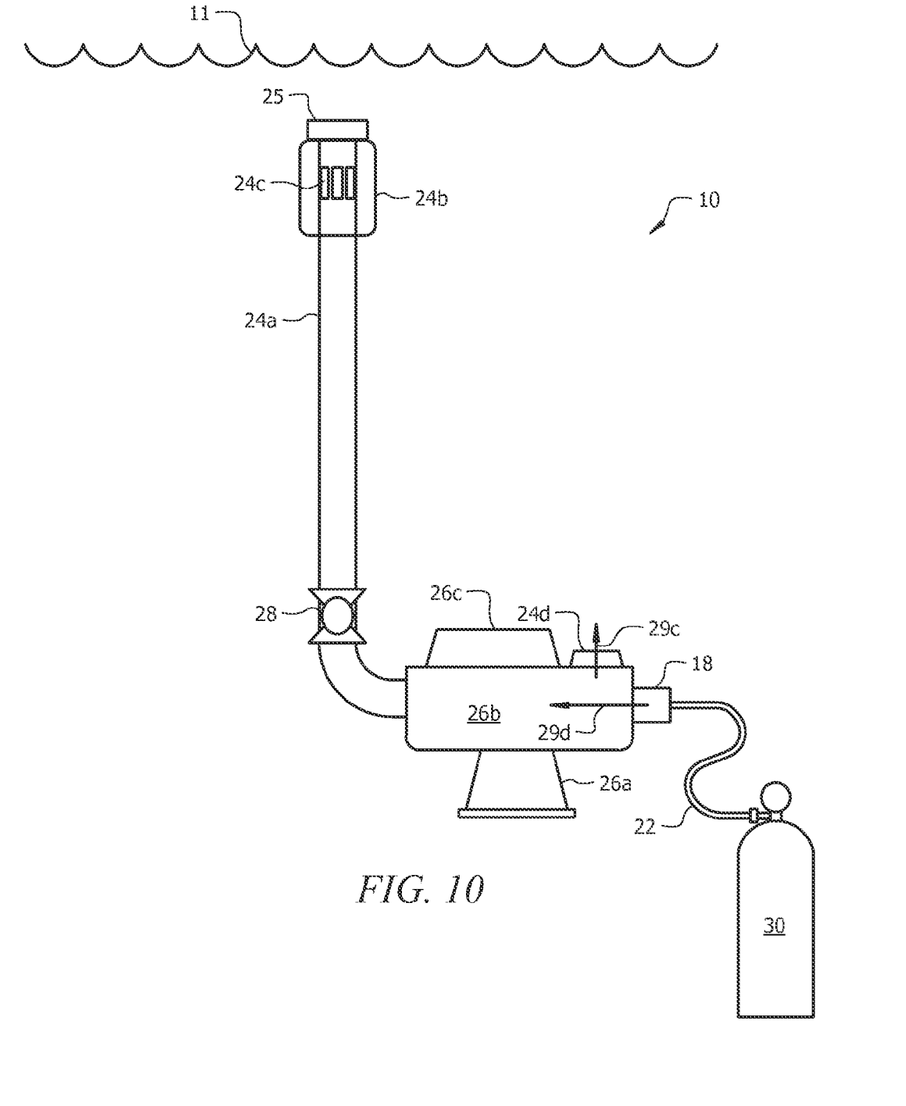
FIG. 10 is a side elevational view of a seventh embodiment.

FIG. 10 depicts the operation of the fifth embodiment of the novel structure when the diver and hence the apparatus is submerged as depicted and valve 28 is closed. Air holes 24c are now closed by float valve 24b. Exhaust valve 24d opens when the diver exhales as indicated by directional arrow 29c because the exhaled air cannot flow through closed valve 28 and the pressure of the exhaled air is sufficient to overcome the bias of exhaust valve 24d that holds it normally closed. Regulator valve 18 opens for the same reason, i.e., inhaled air cannot flow through closed valve 28 so the suction created by an inhalation overcomes the bias that holds regulator valve 18 closed and inhaled air flows into breathing chamber 26b as indicated by directional arrow 29d and air flows from SCUBA tank 30 through air hose 22.

Figure 11A:
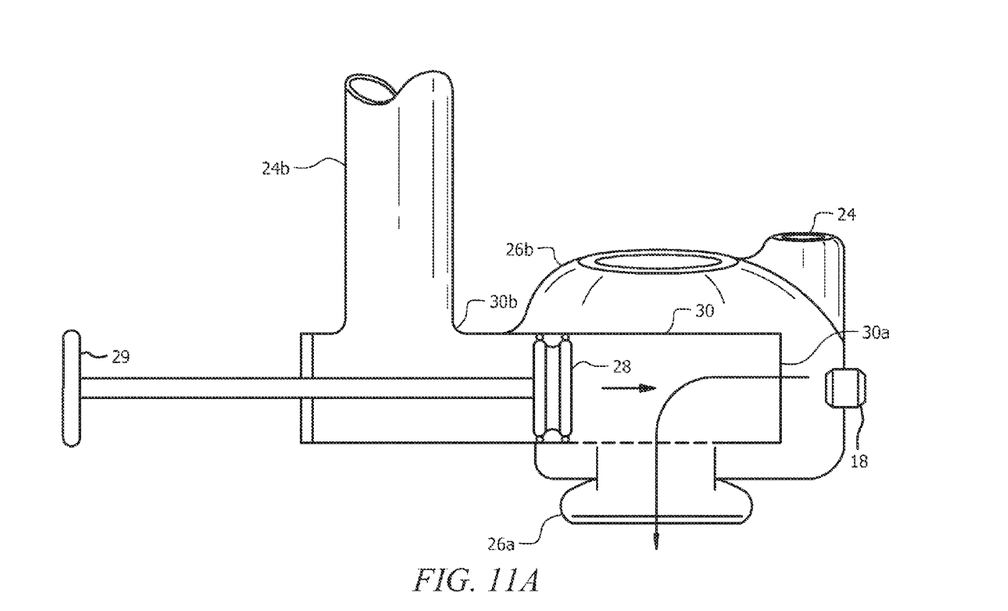
FIG. 11A is a side elevational view of the seventh embodiment when a user is submerged below snorkeling depth.
Figure 11B:
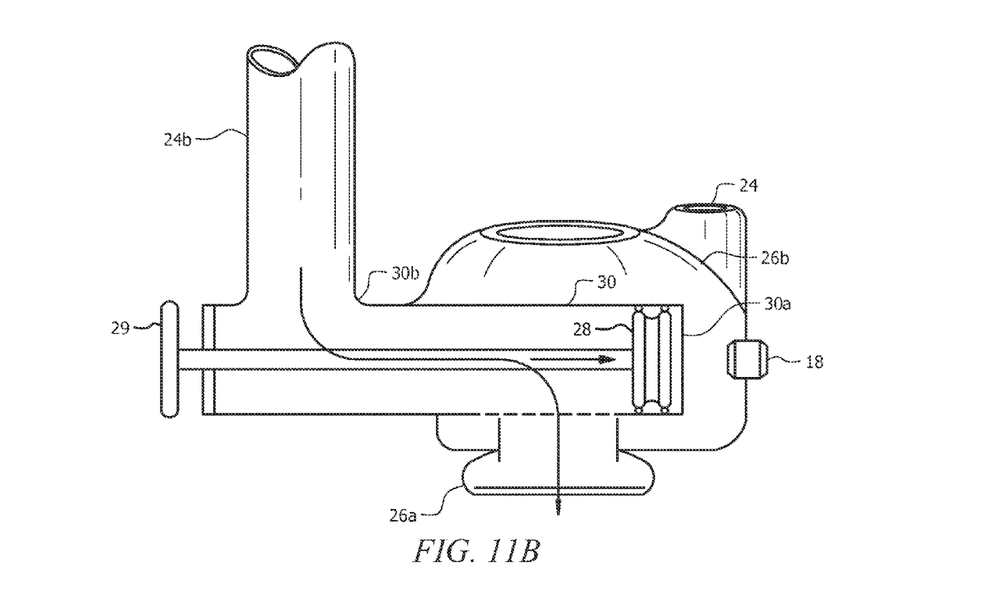
FIG. 11B is a side elevational view of the seventh embodiment when a user is at snorkeling depth.

FIGS. 11A and 11B depict a sixth embodiment where piston 28 is slideably mounted in cylinder 30, having closed end 30a and open end 30b, which is positioned within breathing chamber 26b. When piston 28 is in the FIG. 11A position, air from snorkel tube 24b is blocked and mouthpiece 26a is in open fluid communication with a compressed air tank through regulator valve 18. When piston 28 is in the FIG. 11B position, air from the compressed air tank is blocked is blocked and mouthpiece 26a is in open fluid communication with snorkel tube 24a. The user moves the piston to the desired position by pushing or pulling on handle 28c which is connected to piston 28. Mouthpiece 26a is in open fluid communication with the compressed air tank when handle 29 is in its "out" position as depicted in FIG. 11A and said mouthpiece is in open fluid communication with snorkel tube 24b when handle 29 is in its "in" position as depicted in FIG. 11B.

Figure 12A:
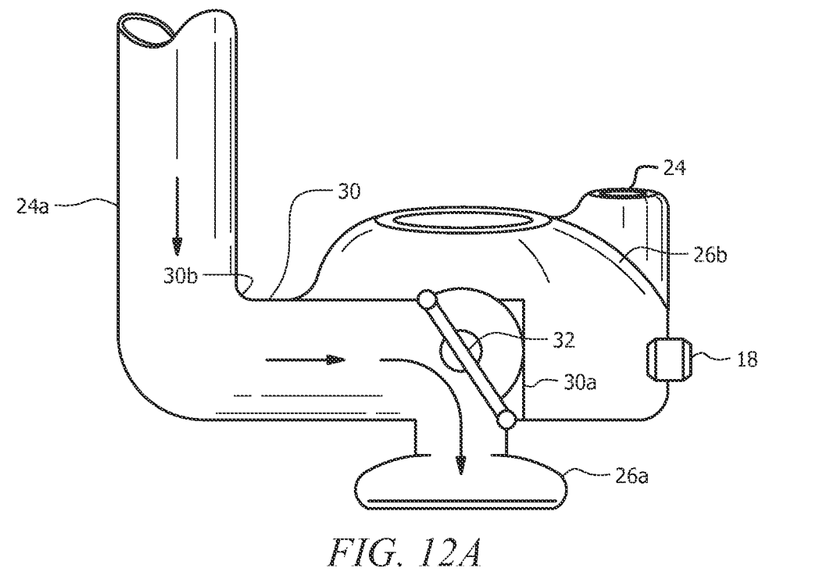
FIG. 12A is a side elevational view of the seventh embodiment when a user is at snorkeling depth.
Figure 12B:
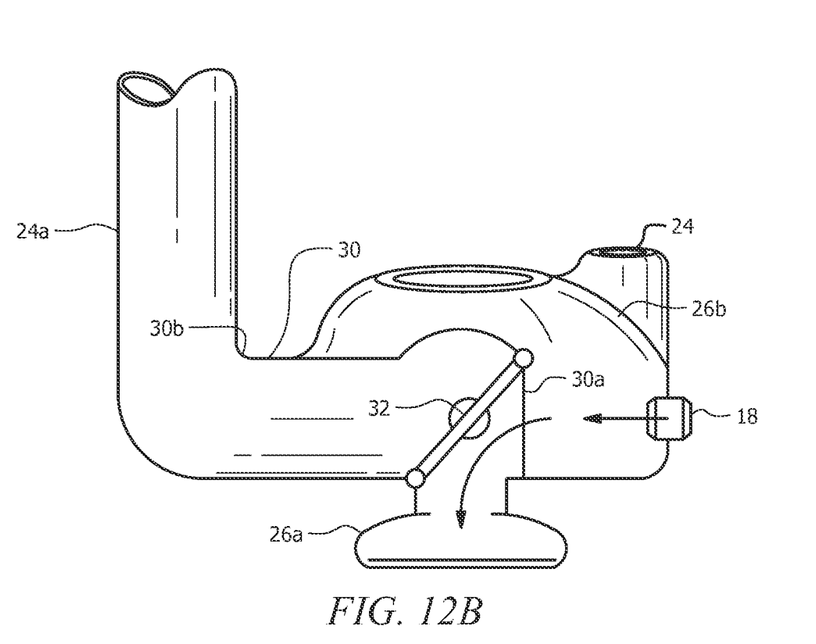
FIG. 12B is a side elevational view of the seventh embodiment when a user is submerged below snorkeling depth.

FIGS. 12A and 12B depict a seventh embodiment. This embodiment includes a rotatably mounted valve 32. When in its FIG. 12A position, valve 32 blocks air flow from a compressed air tank and permits inhaled air flow from snorkel tube 24b to mouthpiece 26a and exhaled air flow from mouthpiece 26a to snorkel tube 24b. When in its FIG. 12B position, valve 32 blocks air flow from snorkel tube 24a and permits inhaled air flow from a compressed air tank through regulator valve 18 to mouthpiece 26a and exhaled air flow from mouthpiece 26a to exhaust valve 24d.

Figures 13A, 13B:
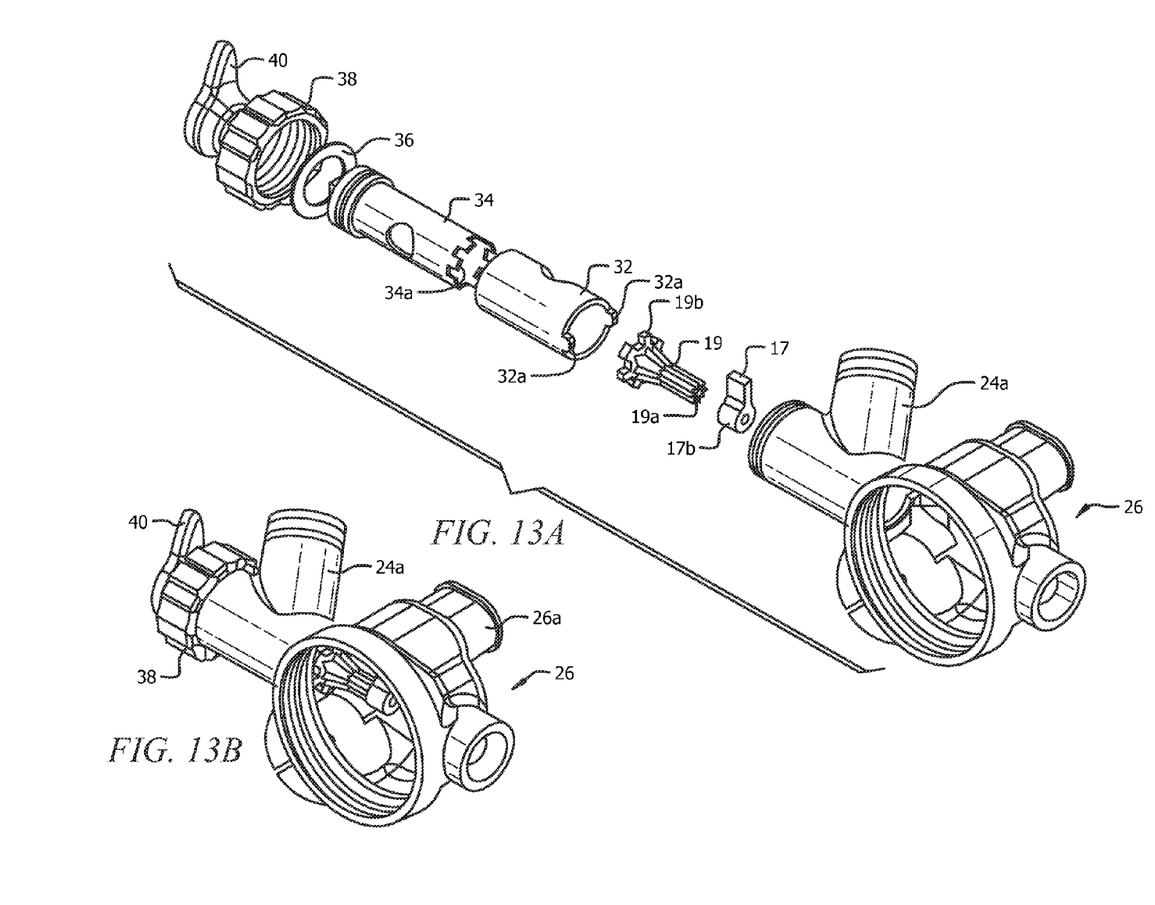
FIG. 13A is an exploded perspective view of an eighth embodiment.
FIG. 13B is a perspective view of the parts depicted in FIG. 13A when in an assembled configuration.

FIGS. 13A and 13B depict an eighth embodiment in exploded and assembled views, respectively. In this embodiment, valve 28 it performs two (2) functions. In a first position, it cuts of the snorkel and engages the auxiliary spring. In a second position it opens the snorkel and disengages the auxiliary spring.

Referring to FIG. 13A, rotation of handle 40 effects conjoint rotation of two-position valve 28 which is connected to or formed integrally with splined shaft 19. This rotation closes the snorkel valve and engages the auxiliary spring. Bushing 32 forms a better seal between rotating valve 28 and snorkel body 24.

Anchor arm 17 having base 17b and splined shaft 19, depicted in FIG. 4, are depicted in FIGS. 13A and 13B to better explain their position in a commercial embodiment. The leading end of shaft 19 is externally splined as at 19a to engage the internal splines formed in base 17b of anchor arm 17 as disclosed above in connection with FIG. 4. The trailing end of shaft 19 is also splined as at 19b and said splines 19b are engaged by tabs 32a formed in the leading end of cylindrical valve bushing 32. Splines 19b are also engaged by tabs 34a formed in the leading end of cylindrical valve core 34 because said cylindrical valve core 34 is slidingly received within the lumen of valve bushing 32 as best understood by comparing FIGS. 13A and 13B.

PTFE washer 36 ensures a watertight seal between the valve and cover 38. Two-position valve 28 and handle 40 are depicted in FIGS. 13A and 13B in the closed position. Rotation of valve handle 40 one hundred eighty degrees (180°) from that position closes said valve.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An apparatus that integrates the operation of a snorkel with a diving regulator, comprising:
    an outer tube having a snorkel aperture, a regulator aperture, and a mouthpiece aperture formed therein;
    said snorkel aperture and said regulator aperture being longitudinally spaced apart and longitudinally aligned with one another;
    said mouthpiece aperture being circumferentially spaced apart from said regulator aperture;
    a lumen of said outer tube being open at a first end and closed at a second end;
    an inner tube having a snorkel aperture, a regulator aperture, and a mouthpiece aperture formed therein;
    said inner tube being rotatably mounted within the lumen of said outer tube;
    a rotatably mounted knob closing a first end of said inner tube;
    an imperforate wall closing a second end of said inner tube;
    said snorkel aperture of said outer tube and said snorkel aperture of said inner tube being in registration with one another when said inner tube is in a first position of rotational adjustment relative to said outer tube;
    said regulator aperture of said outer tube and said mouthpiece aperture of said inner tube being in registration with one another when said inner tube is in a second position of rotational adjustment relative to said outer tube;
    said regulator aperture of said outer tube being closed by an imperforate extent of said inner tube when said inner tube is in said first position of rotational adjustment relative to said outer tube;
    said snorkel aperture of said outer tube being closed by an imperforate extent of said inner tube when said inner tube is in a second position of rotational adjustment relative to said outer tube;
    said mouthpiece aperture of said inner tube and said regulator aperture of said outer tube being in registration with one another when said inner tube is in said second position of rotational adjustment;
    said regulator aperture of said inner tube and said mouthpiece aperture of said outer tube being in registration with one another when said inner tube is in said second position of rotational adjustment; and
    a diving regulator being in open fluid communication with said regulator aperture of said outer tube.

2. The apparatus of claim 1, further comprising:
    said circumferential spacing being about ninety degrees (90°).

3. The apparatus of claim 2, further comprising:
    said first end of said inner tube being closed by the rotatably mounted knob adapted to be rotated by a user of said apparatus.

4. The apparatus of claim 1, wherein the snorkel includes a snorkel tube having a two-position valve that, through connection to a float, automatically opens and closes.

* * * * *